US00PP10261P

United States Patent [19]

Enthoven

[11] Patent Number: Plant 10,261

[45] Date of Patent: Feb. 24, 1998

[54] GERANIUM PLANT NAMED 'MERIPINO'

[75] Inventor: Adrianus W. M. Enthoven, Wateringen, Netherlands

[73] Assignee: Enthoven Breeding B.V., Wateringen, Netherlands

[21] Appl. No.: 760,814

[22] Filed: Dec. 5, 1996

[51] Int. Cl.[6] ..... A01H 5/00

[52] U.S. Cl. ..... Plt./87.12

[58] Field of Search ..... Plt./87.12

*Primary Examiner*—James R. Feyrer
*Assistant Examiner*—Elizabeth C. Kemmerer
*Attorney, Agent, or Firm*—C. A. Whealy

[57] ABSTRACT

A new and distinct cultivar of Geranium plant named 'Meripino', characterized by its rounded and upright growth habit; moderate growth rate and vigor; fast rooting; medium green foliage color with distinct zonation pattern; large umbels with about 30 flowers per umbel; semi-double medium pink flowers; and good weather and stress tolerance.

1 Drawing Sheet

1

The present invention relates to a new and distinct cultivar of Geranium plant, botanically known as *Pelargonium× hortorum*, and hereinafter referred to by the cultivar name Meripino.

The new cultivar is a product of a planned breeding program conducted by the inventor in Wateringen, The Netherlands. The objective of the breeding program was to develop new zonal-type geranium cultivars with semi-double flowers, fast rooting, tolerance to Botrytis, weather resistance, compact plant growth habit, and interesting and unique flower colors.

The new cultivar originated from a cross made by the inventor of two unidentified proprietary seedling selections. The cultivar Meripino was discovered and selected by the inventor as a flowering plant within the progeny of the stated cross in a controlled environment in Wateringen, The Netherlands, in June, 1991.

Plants of the male parent have light pink flowers whereas plants of the new cultivar have medium pink flowers and darker foliage color. Plants of the new cultivar have a distinct zonation pattern on the foliage whereas plants of the female parent do not have a zonation pattern.

Asexual reproduction of the new cultivar by terminal cuttings taken at Wateringen, The Netherlands, has shown that the unique features of this new Geranium are stable and reproduced true to type in successive generations of asexual reproduction.

The following traits have been repeatedly observed and are determined to be the unique characteristics of 'Meripino'. These characteristics in combination distinguish 'Meripino' as a new and distinct cultivar:

1. Rounded and upright growth habit.
2. Moderate growth rate and vigor.
3. Fast rooting.
4. Medium green foliage color with distinct zonation pattern.
5. Large umbels with about 30 flowers per umbel.
6. Semi-double medium pink flowers.
7. Good weather and stress tolerance.

The new Geranium is similar to plants of the cultivar Miro (disclosed in U.S. Plant Pat. No. 9,579) in flower color. However, compared to plants of the cultivar Miro, plants of the new cultivar are more compact; have a darker, more distinct zonation pattern on the foliage; and lighter pink-colored petal margins.

The accompanying colored photographs illustrate the overall appearance of the new cultivar, showing the colors as true as it is reasonably possible to obtain in colored reproductions of this type.

2

The first photograph comprises a top perspective view of a typical potted plant of 'Meripino'.

The second photograph comprises a close-up view of typical leaves of 'Meripino'. Foliage and flower colors in the photograph may appear different from the actual colors due to light reflectance.

The cultivar Meripino has not been observed under all possible environmental conditions. The phenotype may vary somewhat with variations in environment such as temperature and light intensity, without, however, any variance in genotype. The following observations, measurements and comparisons describe plants grown in Wateringen, The Netherlands, under commercial practice in a glass-covered greenhouse with day temperatures of 20C and night temperatures of 18C and light levels of 450 W/m$^2$.

In the following description, color references are made to The Royal Horticultural Society Colour Chart except where general terms of ordinary dictionary significance are used.

Classification:

*Botanical.*—*Pelargonium×hortorum* cv Meripino.

*Commercial.*—Zonal Geranium.

Parentage:

Male parent.—Unidentified proprietary seedling selection.

Female parent.—Unidentified proprietary seedling selection.

Propagation:

*Type cutting.*—Terminal cuttings.

*Time to initiate and develop roots.*—Summer: About 16 days at 20C. Winter: 16 to 20 days at 20C.

*Rooting habit.*—Vigorous, fast to root, freely branching.

Plant description:

*General appearance.*—Rounded and upright growth habit. Appropriate for 10.5 to 12 cm containers. About 12 weeks are required to produce a finished plant from an unrooted cutting.

*Growth rate.*—Moderate.

*Vigor.*—Moderate.

*Plant height.*—Soil level to top of leaves: About 16 cm. Soil level to top of flowers: About 26 cm.

*Branching habit.*—Moderate to low branching with about 3 lateral branches per plant.

*Internode length.*—About 2 cm.

*Foliage description.*—Arrangement: Alternate. Shape: Generally reniform with cordate base. Aspect: Slightly undulating.

*Size.*—Length: 4 to 5 cm. Width: 6.5 to 8.5 cm.

*Texture.*—Velvety, pubescent on abaxial and adaxial surfaces.

*Margin.*—Crenate.

*Zonation.*—Distinct zone, 1 to 1.5 cm in width and about 1 cm from margin.

*Color.*—Abaxial surface: 137A/137B. Adaxial surface: 137C. Zonation, abaxial surface only: 137A/141C.

*Venation pattern.*—Palmate.

*Petiole.*—Length: 6 to 7 cm. Diameter: About 3 mm. Color: 137B/137C.

*Durability to rain, wind and stress conditions.*—Very good.

Flowering description:

*Flowering habit.*—Semi-double flowers arranged in umbels.

*Natural flowering season.*—Spring through to mid-autumn.

*Flower longevity.*—Flowers last about 2.5 weeks on the plant.

*Flowers borne.*—Flower buds develop in apical leaf axils. Umbels are displayed above the foliage.

*Umbels.*—Form: Rounded. Quantity of flowers per umbel: About 30. Diameter: 9 to 10 cm. Depth (height): About 7 cm.

*Flowers.*—Form: Semi-double. Shape: Rounded. Diameter: 4 to 4.5 cm. Depth (height): 1.5 to 2.5 cm. Quantity of petals and petaloids per flower: About 10.

*Petals.13* Shape: Obovate with rounded apex. Arrangement: Rosette, overlapping. Aspect: Flat. Size: Length: 2.2 to 2.5 cm. Width: 1.9 to 2.3 cm. Texture: Satiny, smooth. Margin: Entire. Color: Opened flower, upper petals, abaxial surface, margin: 50D. Opened flower, upper petals, abaxial surface, center: 52D with faint stripes. Opened flower, upper petals, adaxial surface: 52D. Opened flower, lower petals, abaxial surface, margin: 50D. Opened flower, lower petals, abaxial surface, center: 47C/49A. Opened flower, lower petals, adaxial surface: 49C.

*Petaloids.*—Shape: Irregular, generally obovate with rounded apex. Arrangement: Rosette, overlapping. Size: Length: 1.5 to 2.5 cm. Width: About 1.5 cm. Texture: Satiny, smooth. Margin: Entire. Color: 47C/49A.

*Peduncle (umbel stem).*—Angle: Erect. Size: Length: 13 to 17 cm. Diameter: About 5 mm. Texture: Pubescent. Color: Medium green with red tones.

*Pedicel (individual flower stem).*—Angle: Between 45 to 90° from vertical. Size: Length: 2.2 to 3.2 cm. Diameter: 1 to 2 mm. Texture: Pubescent. Color: Green with red tones.

*Flower bud.*—Shape: Elliptic. Size: Length: About 7 mm. Diameter: About 5 mm. Color Light green with slight red tones at base.

*Sepals.*—Shape: Narrowly lanceolate with acuminate apex. Arrangement: Rosette. Quantity: 5. Size: Length: About 1.1 cm. Width: About 3 mm. Texture: Smooth. Margin: Entire. Color: Light green with reddish base.

*Reproductive organs.*—Androecium: Stamen number: 5 to 10. Anther shape: Elongated oval. Anther size: About 2 mm. Pollen color: 171A. Gynoecium: Pistil number: 1. Pistil length: About 8 mm. Stigma shape: Decurrent. Stigma color: 54A. Style length: About 3 mm. Style color: 54C.

Disease resistance: No fungal, bacterial nor viral problems observed under commercial conditions.

Seed Development: Seed production is very rarely observed.

It is claimed:

1. A new and distinct cultivar of Geranium plant named 'Meripino', as illustrated and described.

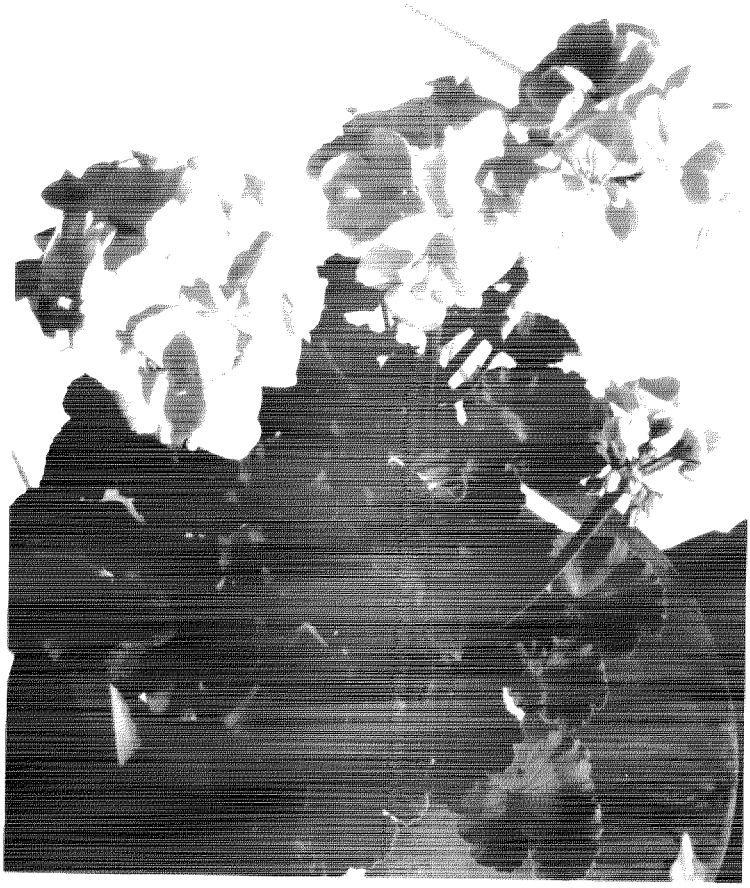
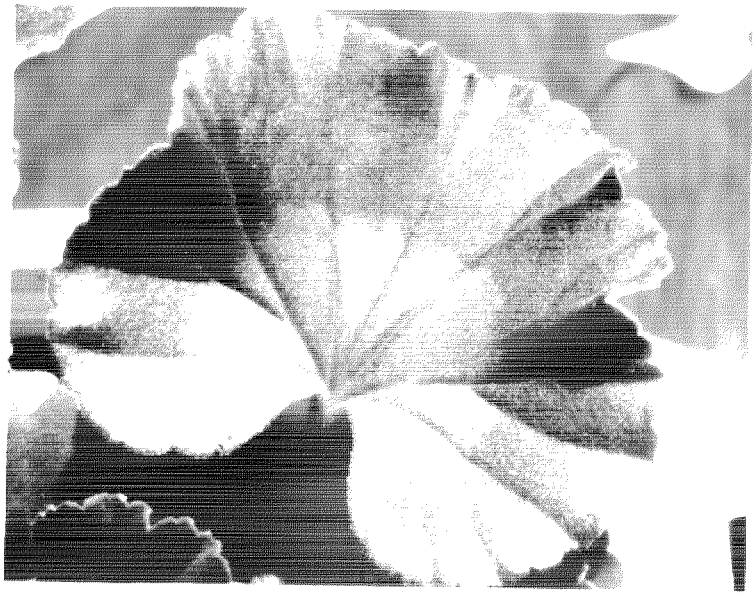

* * * * *